(12) United States Patent
Galloway et al.

(10) Patent No.: US 7,316,698 B1
(45) Date of Patent: Jan. 8, 2008

(54) LOAD-CONTROLLED AUTO-ACTUATED SKIN INCISION DEVICE

(75) Inventors: Edward L. Galloway, Beaumont, TX (US); Eric Petersen, Beaumont, TX (US); Tipton Golias, Beaumont, TX (US)

(73) Assignee: Helena Laboratories, Beaumont, TX (US)

( * ) Notice: Subject to any disclaimer, the term of this patent is extended or adjusted under 35 U.S.C. 154(b) by 691 days.

(21) Appl. No.: 10/628,199

(22) Filed: Jul. 28, 2003

Related U.S. Application Data

(60) Provisional application No. 60/400,999, filed on Aug. 5, 2002.

(51) Int. Cl.
*A61B 17/32* (2006.01)
(52) U.S. Cl. ...................... 606/167; 600/583
(58) Field of Classification Search ............ 606/167, 606/181, 182, 184, 185; 600/583; 604/220
See application file for complete search history.

(56) References Cited

U.S. PATENT DOCUMENTS

| | | |
|---|---|---|
| 4,064,871 A | 12/1977 | Reno |
| 4,535,769 A | 8/1985 | Burns |
| 4,643,189 A | 2/1987 | Mintz |
| 5,314,441 A | 5/1994 | Cusack et al. |
| 5,395,388 A | 3/1995 | Schraga |
| 5,527,333 A | 6/1996 | Nikkels et al. |
| 5,529,581 A | 6/1996 | Cusack |
| 5,584,846 A | 12/1996 | Mawhirt et al. |
| 5,797,940 A | 8/1998 | Mawhirt et al. |
| 5,851,215 A | 12/1998 | Mawhirt et al. |
| 6,221,089 B1* | 4/2001 | Mawhirt .................. 606/181 |
| 6,432,120 B1 | 8/2002 | Teo |

* cited by examiner

*Primary Examiner*—Michael J. Hayes
*Assistant Examiner*—Victor Nguyen
(74) *Attorney, Agent, or Firm*—Egbert Law Offices

(57) ABSTRACT

A skin incision device including a housing having a bottom surface with a slot formed therein, a top positioned on said housing and slidable in a direction toward the bottom surface, a blade pivotally positioned in the housing adjacent said slot, and a spring cooperatively positioned between said top and an interior of the housing. The spring is actuatable by the slidable movement of said top toward the bottom surface of the housing. The spring moves the blade between a pre-actuated position and a post-actuated position.

8 Claims, 3 Drawing Sheets

LOAD-CONTROLLED AUTO-ACTUATED SKIN INCISION DEVICE

RELATED U.S. APPLICATIONS

The present application claims priority from U.S. Provisional Patent Application Ser. No. 60/400,999, filed on Aug. 5, 2002, and entitled "Internal Actuator for Bleeding Time Testing Device".

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to medical devices. More particularly, the present invention relates to devices for incising the skin. In particular, the present invention relates to internal actuators for skin incising devices which apply a controlled load and a constant force during the incising operation. Additionally, the present invention relates to skin incising devices that are used for the purpose of blood acquisition.

BACKGROUND OF THE INVENTION

In the medical field, it is a very common procedure, and often very necessary, to conduct a bleeding time test which measures the time required for the cessation of bleeding following a skin incision. This test is medically important because extended or prolonged bleeding time can be associated with, for example, a lack of or a great excess of platelets, abnormality of platelet function, coating of platelets by specific proteins or foreign materials or the action of certain drugs; e.g., aspirin.

Although the bleeding time test procedure was first described approximately ninety years ago, it did not receive general acceptance until the 1940's at which time the test's sensitivity was increased by making a skin incision on the forearm of the patient while maintaining a blood pressure cuff inflation to maintain venostasis at a standardized level. Using this procedure, a technologist simultaneously starts a stopwatch while making the incision. The emerging blood is then gently blotted every thirty seconds. The cessation of bleeding is defined as the time at which the blotting paper is no longer stained by the emerging blood. This amount of time is generally recorded to the nearest half minute.

Disposable bleeding time devices were first introduced in 1978 to facilitate automation and convenience. These devices improved the acceptance of the test by both the patient and the operator. However, the results were still subject to a variety of technical variables. Additionally, these devices were significantly more expensive than previous methods. This hindered the acceptance of such devices in many countries around the world. Importantly, different disposable devices evolved over time which were functionally quite dissimilar so that the results were not comparable. Thus, standardization remained an elusive goal in bleeding time testing.

An important bleeding time testing device is known as the TRIPLETT™ bleeding time testing device. This was named after the noted physician in blood coagulation and hematopathology, Dr. Douglas Triplett. This device is presently manufactured and sold by Helena Laboratories of Beaumont, Tex. This device met the goal of global standardization in bleeding time testing and utilizes advanced technology at a universally affordable price. This was a product that provided a new level of value to automated, disposable bleeding time devices. This TRIPLETT™ bleeding time testing device was designed to be user and patient friendly, virtually painless, and to mimic the incision motion of the original bleeding time method. The device makes a standardized surgical incision one millimeter deep by five millimeters long for accurate sensitive bleeding time testing. The blade automatically retracts after incisions so as to ensure safety. The device includes a large contact surface that distributes the downward force over a wider area of skin so as to reduce the potential for deep non-standardized cuts. This device is presently subject to patent protection under U.S. Pat. Nos. 5,662,672 and 5,733,300.

Various other U.S. patents have issued relating to such bleeding time testing devices. For example, U.S. Pat. No. 4,064,871, issued on Dec. 27, 1977 to W. J. Reno, teaches a bleeding time testing device that includes a housing having a surface with a slot defining a longitudinal opening into the housing. A blade is mounted within the housing for movement of the blade tip through and along the slot. Biasing springs are provided within the housing to urge the blade through the slot a predetermined distance and along the slot for a predetermined length to control the depth and length of an incision produced with the device. A trigger is provided to initiate movement of the blade along with a safety pin to prevent the inadvertent activation of the device.

U.S. Pat. No. 4,628,929, issued on Dec. 16, 1986 to Intengan et al., describes another type of retractable bleeding time testing device. This device includes a housing, a hammer mechanism pivotally positioned within the housing and having a cam surface, and a self-retracting shuttle supported within the housing and including a cam follower surface. The shuttle is operative to travel in a vertical direction by the movement of the cam surface along the cam follower surface and the force exerted on the shuttle by a first spring extending from the shuttle. A cutting blade is secured to the shuttle and is operative to move out of the housing to make the incision and then to self-retract into the housing. A second spring is operative to exert a force on the hammer to cause it to move along the cam follower surface and to cause the shuttle to travel downwardly thus causing the blade to travel out of the housing to make the incision. The second spring is also operative to move into a locked position to secure the blade within the housing after the blade has retracted back into the housing.

U.S. Pat. No. 5,031,619, issued on Jul. 16, 1991, to F. Pompei, describes a method for determining bleeding time which includes a cutting assembly and a member for providing a compensation factor as a function of the temperature of the patient. The cutting assembly provides an incision of predetermined dimensions for external bleeding therethrough. The compensation member measures temperature of the patient throughout the period of external bleeding and provides a compensation factor as a function of the sensed temperature.

One of the problems associated with the use of the TRIPLETT™ device is that the force applied to actuate the device is off-center from the location at which the blade emerges from the cutting surface. As such, variations of pressures applied to the device can occur. As a result, the bleeding time testing can have a lack of consistent testing.

Angular deflections of the cutting surface can also occur by the off-center application of pressure to the actuator of such cutting device. As such, a need has developed for a device for actuating such bleeding time testing devices such that the pressure of actuation will be directly above the location of the incision.

U.S. Application Ser. No. 60/393,971, filed on Jul. 5, 2002, by the present applicant, describes a constant force actuator for a bleeding time testing device. This constant force actuator is externally applied to an existing bleeding time testing device. The bleeding time testing device includes a body having a bottom surface from which a cutting blade can emerge so as to carry out an incision. The body includes a switch pin actuator that extends outwardly of the top surface in the testing device body. The switch pin is movable between a pre-actuating position and an actuating position. A safety tab is removably positioned between the switch pin actuator so as to retain the switch pin actuator in its pre-actuating position. The safety tab is to be removable so as to enable the testing device to be actuated by moving the switch pin from the pre-actuating position to the actuating position. The cutting blade is cooperative with the switch pin actuator to move outwardly of the bottom surface of the body of the testing device when the switch pin is moved to the actuating position. In this provisional patent application, a constant force device is mechanically attached to the surface of the body of the bleeding time testing device. The constant force device has a housing that is mounted onto the top surface of the bleeding time testing device so as to extend parallel to the bottom surface of the device. A suitable spring clip is provided on the housing so as to allow the actuator housing to be affixed to the body of the bleeding time testing device. A slide frame is mounted on the housing so as to be in slidable relationship to the housing. The slide frame is movable between a pre-activated position to an activated position. In the pre-activated position, the slide frame has a surface which resides against the switch pin actuator in the pre-activated position. A spring is mounted so as to be cooperative with the slide frame so as to urge the slide frame to the actuated position. An actuator button is slidably mounted on the housing so as to be slidable in a direction transverse to the plane of the bottom surface of the bleeding time testing device. When the actuator button is depressed, the spring associated with the slide frame urges the slide frame in a horizontal direction parallel to the bottom surface of the bleeding time testing device and thereby moves the switch pin actuator from the pre-actuating position to the actuating position. The actuator button is positioned directly above the center line of the cutting blade during the incision procedure.

It is an object of the present invention to provide a skin incision device that will not make the incision until a controlled vertical force is applied against the subject tissue.

It is another object of the present invention to provide a skin incision device that removes the variations of force that are applied by different operators at the time the incision is performed.

It is another object of the present invention to provide a skin incision device which allows the actuation force to be easily altered by a modification of a spring for the purpose of providing different actuating forces.

It is a further object of the present invention to provide a skin incision device which can be assembled with no force required to load the components which interact to produce the incision.

It is a further object of the present invention to provide a skin incision device in which the blade is propelled by a designed controlled interaction of internal components which creates a slicing into, across and slicing out of subject tissue for the purpose of minimizing the trauma to the subject tissue.

It is another object of the present invention to provide a skin incision device which reduces the introduction of undesirable components of the skin tissue into the incision area and blood sample.

It is still a further object of the present invention to provide a skin incision device that promotes rapid healing of the incision location.

It is still another object of the present invention to provide a skin incision device which has a concurrent action at the incision which locks the device and prohibits the ability of the device to be reloaded for additional uses.

BRIEF SUMMARY OF THE INVENTION

The present invention is a skin incision device that has a housing having a bottom surface with a slot formed therein, a top positioned on the housing and slidable in a direction transverse to the plane of the bottom surface, a blade pivotally positioned in the housing generally adjacent to the slot, and a spring cooperatively positioned between the top and an interior of the housing. The spring is actuatable by the slidable movement of the top toward the bottom surface. The spring is for moving the blade between a pre-actuated position and a post-actuated position such that at least a portion of the blade extends outwardly of the bottom surface through the slot during the movement between the pre-actuated position and the post-actuated position.

In the present invention, the housing has a generally open end opposite the bottom surface. The housing has sides which extend upwardly from the bottom surface. The top extends over the open end and over at least a portion of the sides of the housing. At least one of the sides of the housing has a barb extending outwardly therefrom. The top has a wall extending the side of the housing. The wall has a first retaining slot formed therein and a second retaining slot formed therein above the first retaining slot. The barb engages the first retaining slot when the spring means is in the pre-actuated position. The barb engages the second retaining slot when the spring means is in the post-actuated position.

In the present invention, the spring includes an actuator spring having an end cooperative with an inner surface of the top and extending downwardly into the housing, and a carriage element positioned within the housing. The actuator spring contacts a surface of the carriage element. The carriage element is movable within the housing for moving the blade between the pre-actuated position and the post-actuated position. The carriage element has one end affixed with the housing. The carriage element has a first jointed area formed thereon. The actuator spring has a opposite end in contact with the first jointed area. The carriage element has an opposite end connected to the blade. The carriage element is positioned in a guide area within the housing. The carriage element has a second jointed area formed thereon of a generally U-shaped construction. One end of the actuator spring is affixed to the inner surface of the top. In the preferred embodiment of the present invention, the actuator spring is a leaf spring. The actuator spring has a knuckle formed at an opposite end thereof. The carriage element also includes a retainer affixed to a surface of the carriage element. The knuckle is received within the retainer when the blade is in the pre-actuated position. The knuckle is separable from the retainer when the top moves toward the bottom surface of the housing.

In the present invention, the blade includes a razor member having a cutting edge and a cam connected to an end of the blade and positioned interior of the housing. The spring is cooperatively connected to the cam so as to pivotally move the razor member between the pre-actuated position and the post-actuated position. The housing has a blade retainer peg formed therein adjacent the slot. The blade is positioned onto the blade retainer peg. The blade is pivotally connected to the cam. The blade has an obround formed therein. The obround is positioned over the blade retainer peg. An abutment member is affixed within the housing and has surface contacting a surface of the cam as the razor member moves between the pre-actuated position and the post-actuated position.

In general, the present invention is a device for making a standard incision in skin tissue for the purpose of blood acquisition. The present invention is, in particular, related to bleeding time testing devices. The present invention is a single-use/disposable device which includes the slot for the purpose of allowing the blade to travel out of the device for the purpose forming the incision and then retracting back into the housing of the device. The movable top travels in a downward motion so as to apply an even pressure against the skin. The spring that is connected to the top is actuated when a controlled load limit is achieved. When a controlled load limit is achieved, the spring will release stored energy into a horizontal motion which transfers that motion onto the carriage element. As a result, the carriage element is moved horizontally. When the carriage element is moved horizontally, the geometry of the cam is introduced onto a fixed position peg. This introduction of the force causes a unique travel response by the carriage element which, in turn, transfers this travel response to the blade. The unique travel response of the blade propels the razor member out of the housing, through the skin, and back into the housing in a very controlled action. This controlled action of the razor member is such the razor member is slicing upon entry into the skin, guided horizontally while at depth, and slicing upon exiting the skin. This action of slicing, both entering and exiting, will minimize the trauma to the skin, will reduce the introduction of undesirable elements of the skin tissue into the incision and blood sample, and will promote the rapid healing of the incision location.

DETAILED DESCRIPTION OF THE INVENTION

Figure 1:
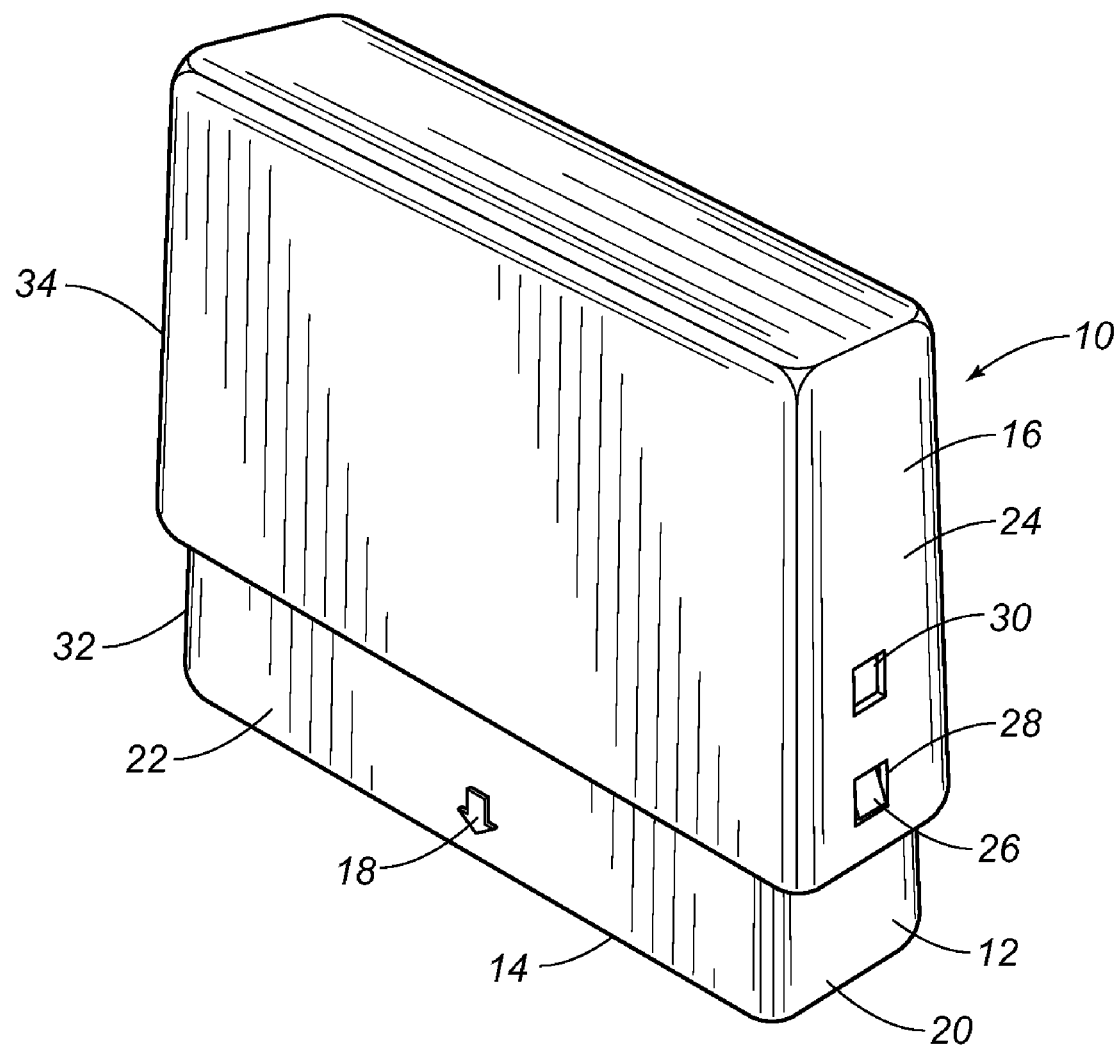
FIG. 1 is an outer perspective view of the skin incision device of the present invention.

Referring to FIG. 1, there is shown the skin incision device 10 in accordance with the teachings of the preferred embodiment of the present invention. The skin incision device 10 includes a housing 12 having a bottom surface 14 and atop 16 slidably positioned on the housing 12. The top 16 is slidable in a direction transverse to a plan of the bottom surface 14. An indicator arrow 18 indicates the centerline of travel of the razor blade.

As will be described hereinafter, the housing 12 will have a generally open end opposite the bottom surface 14. The housing 12 has sides 20 and 22 extending upwardly from the bottom surface 14. The top 16 extends over the open end of the housing 12 and has a wall 24 extending over at least a portion of the side 20 of the housing 12. The side 20 has a barb 26 extending outwardly therefrom. The wall 24 has a first retaining slot 28 and second retaining slot 30 formed above the first retaining slot 28. As can be seen in FIG. 1, the barb 26 engages the first retaining slot 28.

In FIG. 1, the device 10 is shown in its pre-actuated position. Ultimately, the bottom surface 14 will be placed upon the surface of the skin and the top 16 will be pressed downwardly toward the bottom surface 14. As a result, the barb 26 will free itself from the first retaining slot 28. When the device 10 has incised the skin and the blade is retained in its post-actuated position, the barb 26 will then be retained within the second retaining slot 30. As a result, the barb 26 prevents reuse of the device 10. Within the concept of the present invention, it is important to note that another barb can also be placed on the opposite side 32 of housing 12 so as to suitably engage corresponding retaining slots formed on the opposite wall 34 of the top 16.

Figure 2:
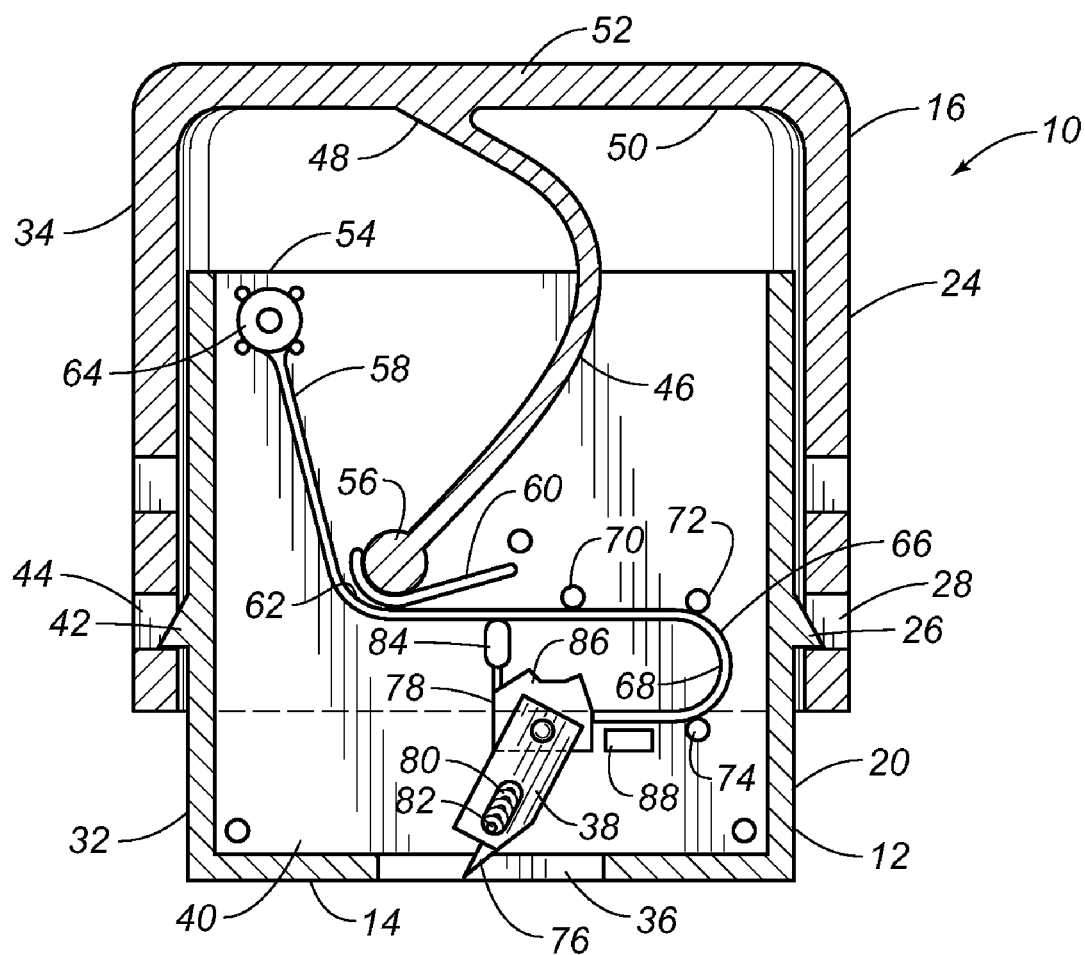
FIG. 2 is a cross-sectional view of the skin incision device of the present invention as shown in its pre-actuated position.

FIG. 2 shows a cross-sectional view of the device 10 of the present invention. In particular, in FIG. 2, it can be seen that the housing 12 has a slot 36 formed on the bottom surface 14 thereof. A blade 38 is positioned in the interior 40 of the housing 12 generally adjacent to the slot 36 and to the bottom surface 14. The housing 12 also has a side 20 extending upwardly from the bottom surface 14 and another side 32 extending upwardly from the bottom surface 14. A barb 26 is secured to the side 20 of housing 12. Another barb 42 is secured to the side 32 of housing 12. As can be seen in FIG. 2, the barb 26 engages the first retaining slot 28 on the wall 24 of top 16. The barb 42 engages the first retaining slot 44 formed on the wall 34 of the top 16. As a result, the top 16 will reside in its pre-actuated position.

In FIG. 2, it can be seen that an actuator spring 46 has an end 48 affixed to the inner surface 50 of the top 52 of housing 16. The actuator spring 46 is a type of leaf spring which will extend downwardly in an arcuate manner through the open end 54 of the housing 12. The opposite end of the actuator spring 46 has a knuckle 56 formed thereon. The actuator spring 46 can be suitably change, replace, altered, or otherwise manipulated so as to exert greater or lesser forces within the interior of housing 12.

A carriage element 58 is positioned within the housing 12. The actuator spring 46 is illustrated as being received within a retainer 60 secured at a first jointed area 62 on the carriage element 58. The first jointed area 62 is a low shear, high tension joint. One end of the carriage element 58 is affixed to a pin 64 on the interior of housing 12.

The carriage element 58 has a unique configuration within the housing 12. In particular, the carriage element 58 includes a second jointed area 66 of a U-shaped construction received within a guide area 68. Guide area 68 is defined by pegs 70, 72 and 74. The end of the carriage element 58 is connected to the blade 38 so as to properly manipulate the blade, as will be described hereinafter. In the pre-actuated position, as shown in FIG. 2, the knuckle 56 of the actuator spring 46 is received within the retainer 60 so as to exert a desired force on the first jointed area 62 of the carriage element 58. As a result, the blade 38 will be in its pre-actuated position entirely interior the housing 12 and adjacent to the slot 36.

The blade 38 includes a razor member 76 formed at a lower end of the blade 38. Additionally, a cam 78 is secured in pivotal relationship to the blade 38. An obround 80 is formed in the blade 38 so as to be in generally pivotal and slidable relationship with a blade retainer peg 82. An abutment member 84 is positioned within the housing 12 generally adjacent to the upper surface 86 of the cam 78. In normal use, the abutment member 84 will reside adjacent to one edge of the surface 86 of cam 78. When the device is suitably actuated, the abutment member 84 will travel along the surface 86 of cam 78 so as to cause the downward and incising movement of the blade 38. A bounce control peg 88 is also formed within the interior of housing 12 so as to act as a guide for the carriage element 58 and to prevent outward bouncing of the razor member 76 when the device is actuated.

Figure 3:
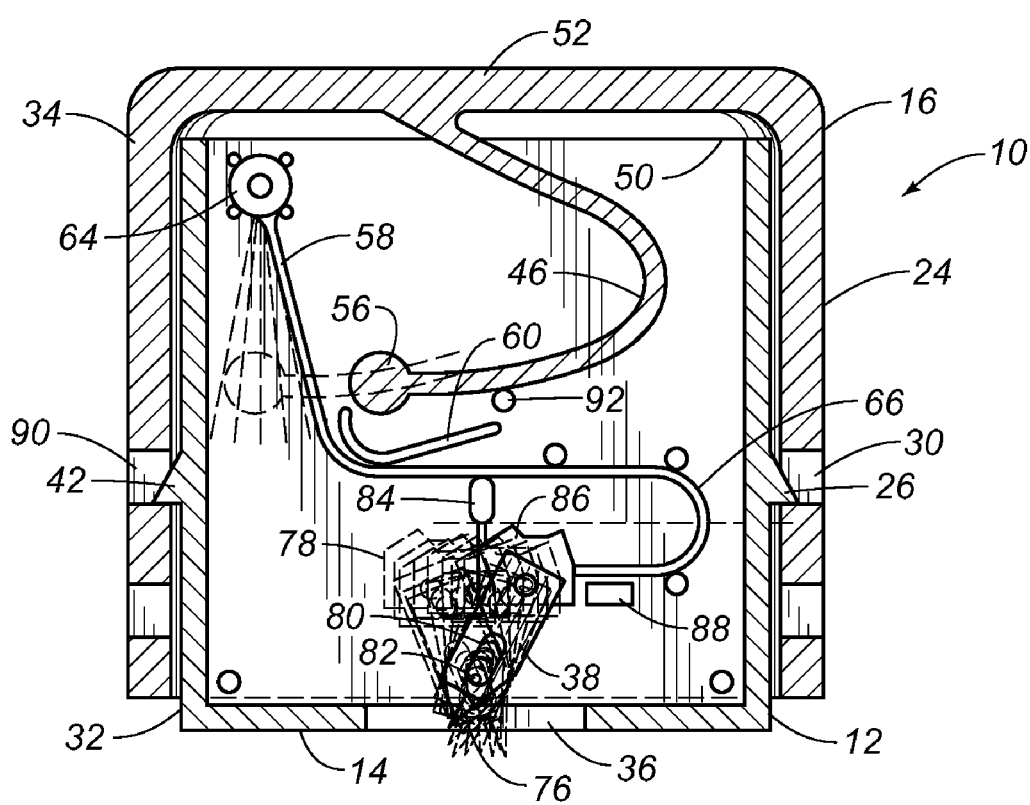
FIG. 3 is a cross-sectional view of the skin incision device of the present invention showing the device in its movement between the pre-actuated position and the post-actuated position.

FIG. 3 shows the device 10 in its movement between pre-actuated position and the post-actuated position. In particular, in FIG. 3, it can be seen that the top 16 has been pressed downwardly upon the housing 12. As a result, the barbs 26 and 42 will be received within the respective second retaining slots 30 and 90 of the top 16.

Importantly, in FIG. 3, it can be seen that the actuator spring 46 has been suitably compressed by the downward movement of the top 16 relative to the bottom surface 14 of housing 12. The actuator spring 46 will deflect by its contact with abutment peg 92. The cantilever movement caused by the peg 92 will cause the knuckle 56 to be separated from the retainer 60. Once released, the knuckle 56, in combination with the actuator spring 46, will exert a force on the carriage element 58 so as to cause the carriage element 58 to move toward the side 32 of housing 12. This will also cause the carriage element 58 to press the opposite end inwardly. As a result, the surface 86 of cam 78 will travel along the abutment member 84 so as to create the outward movement of the razor member 76 of blade 38. The bounce control peg 88 will prevent any accidental bounce or resilient movement of the razor member 76 outwardly of the slot 36.

The operation of the present invention allows for a designed controlled force to be achieved. The top 16 will travel vertically over the housing 12. The actuator spring 46 is restrained at one end by contact with the inner surface 50 of the upper surface 52 of top 16. The opposite end of the actuator spring 46 is in contact with the top surface of the carriage element 58. The top 16 will continue to travel downwardly and the vertical application force is retained in the actuator spring 46. At a designed vertical pre-determined force, which is achieved as a function of distance traveled and spring flexing, the actuator spring 46 makes contact with the actuation peg 92. When contact is made between the actuator spring 46 and the abutment peg 92, the operator can continue to push down on the top 16. As the top 16 continues to travel downwardly after contact with the actuation peg 92, the peg 92 causes the knuckle 56 to rotate out of the retainer 60. When the restrained knuckle 56 of the actuator spring 46 relocates past the top edge of the retainer 60, the centerline of knuckle 56 is higher than the top edge of the retainer 60. The vertical pre-actuation force is released in a horizontal motion, as shown in FIG. 3. This is controlled by the contact between the actuator spring 46 and the top edge of the retainer 60.

The action described hereinbefore illustrates that a vertical force is appropriately transformed into a horizontal force on the interior of the housing 12. The knuckle 56 of actuator spring 46 will begin to travel toward the nearest side 32 of the housing 12. As the knuckle 56 travels horizontally, it will contact the carriage element 58. In this encounter, the horizontal force will overpower one of the two, low shear/high tension joints 62 and 66 that are designed onto the carriage element 58. When the horizontal force overpowers the jointed area of the carriage element 58, the carriage element 58 begins to travel in a horizontal direction. The horizontal travel of the carriage element 58 is controlled by the various support pegs 70, 72 and 74 which define a guide path within the housing 12. Once the carriage element 58 begins to travel horizontally, the cam 78 is forced to move in two directions simultaneously (i.e. vertically and horizontally) in order to release the force inputted into the carriage element 58 by the actuator spring 46. The carriage element 58 is allowed to move vertically as a designed function of the second low shear/high tension joint 66 at the far right side of the carriage element 58. As the carriage element 58 travels horizontally and vertically, one end of the blade 38 is carried along with the carriage element 58. The surface 86 of cam 78 reacts with the abutment member 84 so as to move the blade 38 through a controlled horizontal and vertical motion. The blade 38 is allowed to move vertically by means of an obround 80 located on the body of the blade 38. The blade 38 is controlled front to back by a shoulder entrapment designed into the blade retainer peg 82. The carriage element 58 travels horizontally and vertically until such time as the energy is totally released from the interaction of the actuator spring 46 with the carriage element 58 or until the carriage element 58 is trapped against the side 32 of housing 12. As such, the blade 38 is propelled through a horizontal/vertical trajectory out of and back into the slotted opening 36 at the bottom surface 14 of housing 12. When this event occurs, a controlled slicing into, across and out of the skin should occur. A concurrent event also occurs at the same time. As described in previously, the barbs 26 and 42 will now engage the second retaining slots 30 and 90 on the walls 24 and 34 of the top 16. As a result, the top 16 will be restrained in a fixed condition which prohibits reuse of the device.

The foregoing disclosure and description of the invention is illustrative and explanatory thereof. Various changes in the details of the illustrated construction can be made within the scope of the present invention without departing from the true spirit of the invention. The present invention should only be limited by the following claims and their legal equivalents.

We claim:

1. A skin incision device comprising:
   a housing having a bottom surface with a slot formed therein;
   a top positioned on said housing, said top being slidable in a direction transverse to a plane of said bottom surface;
   a blade pivotally positioned in said housing generally adjacent said slot, said blade having a pre-actuated position and a post-actuated position; and
   a spring means cooperatively positioned between said top and an interior of said housing, said spring means being actuatable by the slidable movement of said top toward said bottom surface, said spring means for moving said blade between said pre-actuated position and said post-actuated position such that at least a portion of said blade extends outwardly of said bottom surface through said slot during the movement between said pre-actuated position and said post-actuated position, said spring means comprising:

an actuator spring having an end cooperative with an inner surface of said top and extending downwardly into said housing; and a carriage element means positioned within said housing, said actuator spring contacting a surface of said carriage element means, said carriage element means moveable within said housing for moving said blade between said pre-actuated position and said post-actuated position, said carriage element means comprising:

a carriage element having one end affixed within said housing, said carriage element having a first jointed area formed therein, said actuator spring having an opposite end in contact with said first jointed area, said carriage element having an opposite end connected to said blade, said carriage element positioned in a guide area within said housing, said carriage element having a second jointed area formed thereon of a generally U-shaped construction, said end of said actuator spring affixed to said inner surface of said top, said actuator spring being a leaf spring, said actuator spring having a knuckle formed at an opposite end thereof, said carriage element means further comprising:

a retainer affixed to a surface of said carriage element, said knuckle received within said retainer when said blade is in said pre-actuated position, said knuckle being separable from said retainer when said top moves toward said bottom surface of said housing.

2. The device of claim 1, said housing having a generally open end opposite said bottom surface, said housing having sides extending upwardly from said bottom surface, said top extending over said open end and over at least a portion of said sides of said housing.

3. The device of claim 2, at least of one said sides of said housing having a barb extending outwardly therefrom, said top having a wall extending over a portion of the side of said housing, said wall having a first retaining slot formed therein and a second retaining slot formed therein above said first retaining slot, said barb engaging said first retaining slot when said spring means is in said pre-actuated position, said barb engaging said second retaining slot when said spring means is in post-actuated position.

4. The device of claim 2, said blade comprising:
a razor member having a cutting edge; and
a cam connected to an end of said blade and positioned interior of said housing, said spring means being cooperatively connected to said cam so as to pivotally move said razor member between the pre-actuated position and the post-actuated position.

5. The device of claim 4, said housing having a blade retainer peg formed therein adjacent said slot, said blade positioned onto said blade retainer peg, said blade being pivotally connected to said cam.

6. The device of claim 5, said blade having an obround formed therein, said obround positioned over said blade retainer peg.

7. The device of claim 5, further comprising:
an abutment member affixed within said housing and having a surface contacting a surface of said cam as said razor member moves between the pre-actuated position and post-actuated position.

8. A skin incision device comprising:
a housing having a bottom surface with a slot formed therein;
a top positioned on said housing, said top being slidable in a direction transverse to a plane of said bottom surface;
a blade pivotally positioned in said housing generally adjacent said slot, said blade having a pre-actuated position and a post-actuated position; and
a spring means cooperatively positioned between said top and an interior of said housing, said spring means being actuatable by the slidable movement of said top toward said bottom surface, said spring means for moving said blade between said pre-actuated position and said post-actuated position such that at least a portion of said blade extends outwardly of said bottom surface through said slot during the movement between said pre-actuated position and said post-actuated position, said housing comprising:
a front panel; and
a back panel having a plurality of pegs extending toward said front panel, said plurality of pegs defining a guide path for said spring means.

* * * * *